United States Patent [19]

Hanson

[11] Patent Number: 4,492,573
[45] Date of Patent: Jan. 8, 1985

[54] ORTHODONTIC BRACKET

[75] Inventor: Gustaf H. Hanson, Hamilton, Canada

[73] Assignee: Augusta Developments Inc., Hamilton, Canada

[21] Appl. No.: 593,222

[22] Filed: Mar. 27, 1984

[51] Int. Cl.$^3$ .............................................. A61C 7/00
[52] U.S. Cl. ......................................... 433/11; 433/14
[58] Field of Search ............................. 433/11, 20, 14

[56] References Cited

U.S. PATENT DOCUMENTS 4,144,642  3/1979  Wallshein ............................. 433/11
4,197,642  4/1980  Wallshein ............................. 433/11

Primary Examiner—Robert Peshock
Attorney, Agent, or Firm—Hirons, Rogers & Scott

[57] ABSTRACT

A new orthodontic bracket comprises a bracket body with a mesial-distal slot for the reception of an arch wire and a resilient retainer member for retaining the arch wire in the slot, the retainer member being movable on the bracket body in the occlusal-gingival directions between a slot-closed position and a slot-open position. When in the slot-closed position the end of the part of the retainer member which closes the slot extends into a mesial-distal extending retainer slot in the gingival wall of the arch wire slot so that movement of the retainer member end in the labial direction is limited by its engagement with the lingual wall of the retainer slot. The wall that is engaged by the retainer member end preferably in narrower than the bracket body and may comprise a small piece of the spring material used for the retainer member welded to the bracket body. The engaging faces of the retainer member and the retainer slot may be inclined to retain the retainer member in the slot-closed position. The small piece may extend gingivally from the body to provide a tie wing that can receive tie wires and elastics when required.

12 Claims, 4 Drawing Figures

ORTHODONTIC BRACKET

FIELD OF THE INVENTION

The present invention is concerned with improvements in or relating to orthodontic brackets that are employed in procedures for applying corrective moving forces to teeth.

PRIOR ART REVIEW

It is now almost universal practice in orthodontic procedures that each tooth to be moved has a bracket fastened thereto, the brackets being connected together by a thin springy arch wire that applies the required forces thereto. Originally this bracket was fastened to a tooth band that was mounted around the tooth but increasingly, with the development of suitable cement systems, the brackets are welded or otherwise fastened to a bonding pad which is cemented directly to an etched surface of the tooth.

There is disclosed and claimed in my U.S. Pat. No. 3,772,787, issued Nov. 20, 1973, the disclosure of which is incorporated herein by this reference, an orthodontic bracket comprising a bracket body having a mesial-distal extending arch wire slot opening to the labial surface; a U-shaped retainer member of high strength spring material is mounted on the bracket body, the retainer member being in embracing sliding engagement with the body. The retainer member is movable with said embracing sliding engagement on the body between two positions in which the slot labial side opening is respectively open and closed, means being provided for positively retaining the member in at least the said slot-closed position.

There is disclosed and claimed in my U.S. Pat. No. 4,248,588 the disclosure of which also is incorporated herein by this reference, an orthodontic bracket wherein the retainer member labial portion is shaped to protrude in a slot-closed position into the arch wire slot, whereby movement of the retainer member away from the slot-closed position toward the slot-open position takes place against the resilience of the retainer member, since the arms of the U-shaped member are spread apart in moving the said protruding labial portion out of the arch wire slot.

The use of the brackets of these inventions is found to result in greatly expedited procedures, owing to the elimination of the previously-used tie wires that must be individually tied in the mouth and carefully severed and bent so as not to leave sharp ends protruding. Changes in arch wire required during the two-three year course of the average procedure are also greatly expedited, since they require merely the retainer members to be quickly snapped to the open position, the wire changed, and then the retainer members to be quickly returned to the closed position, so that there is a corresponding marked reduction in patient discomfort. There is also a considerable reduction in the amount of manual dexterity required of the orthodontist in the performance of these procedures, reduction of the need for chair-side assistance, as well as a considerable saving of time resulting in greater productivity. A cosmetic advantage is also obtained in that it has been found the brackets can be made smaller than hitherto which, together with the elimination of the somewhat unsightly and potentially uncomfortable tie wires, results in an improved appearance of the patient.

The orthodontic brackets of these inventions are now in commercial production and are distributed and sold as the "Hanson SPEED System" (Trade Mark).

One of the unusual problems involved in the practical design of orthodontic brackets is that it is normal to work from enlarged drawings, commonly 100 times enlarged (100×), and it is correspondingly difficult from visual examination to ensure that the part represented by the drawing will function as intended when produced in "full" size, and precise engineering calculation frequently is required. For example, a number of drawings of proposed orthodontic brackets illustrate members which are so thin that, in actual size, even with the highest modulus metals commercially available, they are unlikely to perform their intended function, or even be capable of manufacture. Again, with my own brackets, although spring stainless steel of very high modulus is used for the production of the retainer members, they are stressed surprisingly close to the elastic limit of the metal as they are moved between slot-open and slot-closed positions, and the amounts of extra force and displacement required to exceed the elastic limit is relatively small. Once the elastic limit has been exceeded then of course the retainer member no longer functions successfully as such, and the bracket must be replaced, since it is not usually convenient for the orthodontist to attempt to replace the spring retainer member "in situ", especially since the operation of mounting the retainer member on the bracket body brings it so close to the elastic limit that considerable care must be taken to ensure against this happening.

Another possibility of spring failure arises in operation if a stiff arch wire is used that protrudes too far from the mesial-distal slot, but the orthodontist forces the retainer member down and outwards to embrace the wire, which is sufficiently strong to over-displace the spring. Moreover, it has been found possible to increase the efficiency and applicability of the brackets by angling the arch wire slot in the mesial-distal plane, permitting a straighter arch wire to be used. However, such brackets are able to apply intense labially-directed forces to one edge only of the retainer member, namely the edge at which the slot and the arch wire are toward the labial, with consequent higher possibility of overstressing the spring retainer member in the labial direction.

It is the principal object of the invention to provide an orthodontic bracket including means for protecting the retainer member while in slot-closed position against exceeding the elastic limit of the material thereof.

It is a more specific object to provide a bracket with which the orthodontist is provided with some positive means to avoid exceeding the allowable limit of labial deflection of the retainer member and consequent escape of the arch wire from the slot.

In accordance with the present invention there is provided an orthodontic bracket comprising a bracket body having lingual, labial, gingival, occlusal, distal and mesial surface portions and a mesial-distal extending arch wire slot opening to the labial surface portion, and a retainer member of resilient material having labial and lingual portions in embracing sliding engagement with corresponding labial and lingual surface portions of the body, the retainer member being movable on the body between two positions in which the open labial side of the slot is respectively open and closed, wherein the mesial distal extending slot is provided in its gingival surface immediately adjacent to the labial bracket surface with a mesial distal extending retainer against which the end of the retainer member labial portion can engage when in slot-closed position to prevent labial movement of the thus engaged retainer member end of more than a predetermined extent.

The said retainer can be constituted by a slot formed in the gingival surface of the mesial distal extending slot, or by a separate piece of metal fastened to the bracket body.

Particular preferred embodiments of the invention will now be described, by way of example, with reference to the accompanying diagrammatic drawings wherein.

Similar parts are given the same reference number in all the Figures of the drawings.

Figure 1:
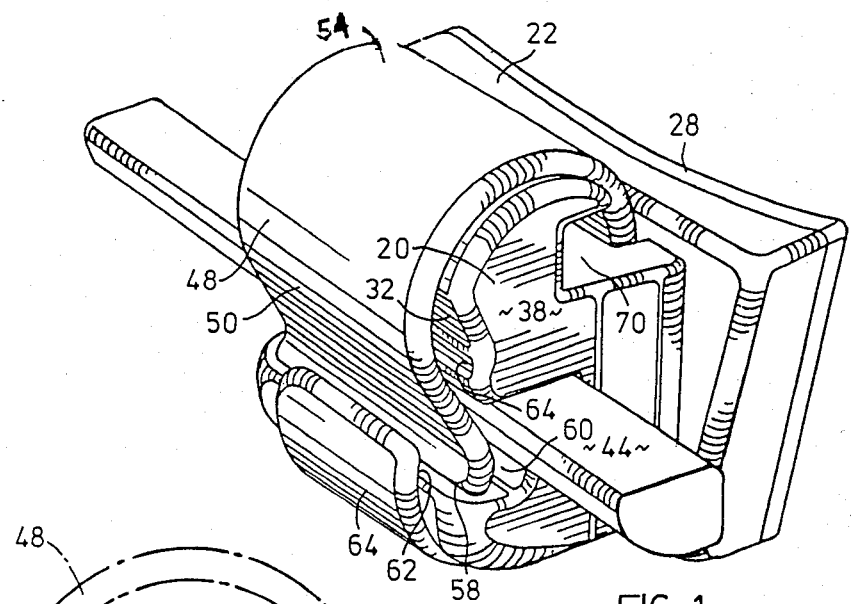
FIG. 1 is a perspective view of a first embodiment.

Each bracket comprises a body 20 which must be mounted on the respective tooth, either by the prior art method of attaching it to a tooth-embracing band (not illustrated) or as shown herein by cementing it directly to the tooth. Thus, the body is provided with a cementing pad 22 which covers the bracket lingual surface 24 and in turn provides a lingual surface 26 which, to facilitate adherence of the cement, is formed by a sintered layer 28 of fine metal powder, as described and claimed in my application Ser. No. 06/486,159, filed Apr. 18, 1983, the disclosure of which is incorporated herein by this reference.

The cement-receiving surface provided by the sintered layer 28 approximates more closely to that of the etched tooth surface to which the bracket is cemented.

For convenience in description, the exterior surface of the bracket body 20 is regarded as comprising a labial surface portion 32, occlusal and gingival surface portions 34 and 36 respectively connected by the labial portion, and two spaced mesial-distal surface portions 38, also connected by the labial portion. The lingual surface portion 24 opposite to the labial portion also joins the occlusal and gingival portions and the two mesial-distal portions. The body surface is smoothly contoured so that adjoining surface portions merge with one another with no specific demarcation junction between them.

Figure 2:
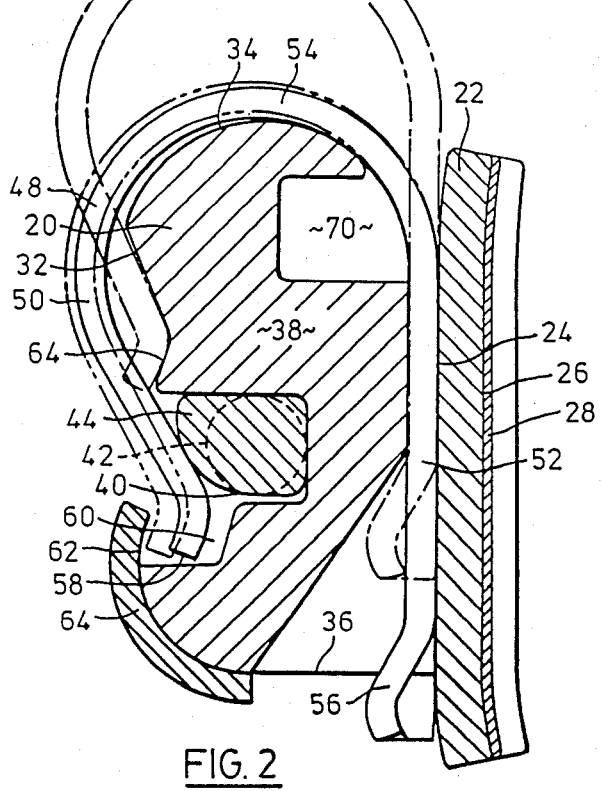
FIG. 2 is a plane section of the bracket of FIG. 1 taken on the line 2—2 of FIG. 1, with the retainer member shown in different positions.

The body is provided with a mesial-distal extending slot 40 of rectangular cross-section opening in the labial surface portion 32 and receiving an arch wire. In FIG. 2 of the drawing a round cross-section arch wire 42 is illustrated as well as the special cross-section wire 44 described and claimed in my U.S. Pat. No. 4,386,909, issued June 7, 1983, the disclosure of which is incorporated herein by this reference. It is of course part of the expertise of the orthodontist to select a wire of appropriate cross-section and dimensions from the many different ones available, depending upon the forces that are required to be applied to the tooth to be moved.

Means for retaining the arch wire in the slot, while permitting relative movements in the required directions between the bracket and the arch wire, comprise a retainer member 48 of thin flat springy stainless steel, shaped to embrace the body 20 and to conform closely while in the slot-closed position, illustrated for example in solid lines in FIG. 2, with the labial, occlusal and lingual portions thereof. For convenience in description the retainer member will be regarded as comprising opposed labial and lingual portions 50 and 52 respectively, each in embracing sliding engagement with the respective bracket body portion, and a connecting occlusal portion 54. As with the body, these different portions of the retainer member merge smoothly into one another with no specific line of demarcation between them. Referring to FIG. 2, the retainer member is movable by sliding and embracing movement on the body between a slot-open position illustrated in broken lines to the above-mentioned slot-closed position illustrated in solid lines.

The retainer member lingual portion 52 is relatively straight so as to guide the retainer member for corresponding straight movement between its two end positions, and terminates in a free end 56 which is dimpled to prevent the retainer member being moved beyond the slot-open position off the bracket. The occlusal portion 54 is approximately semi-circular, while the labial portion 50 immediately adjacent to the occlusal portion is concave toward the body in conforming closely thereto as described. The remaining part of the labial portion that terminates in a free end 58 is relatively straight for most of its length and intrudes deeply into the slot 40. The part of the labial portion including the immediately adjacent to the free end 58 is bent or inclined toward the labial for a reason that will be described below.

The bracket body is also provided with a mesial-distal extending retainer slot 60 opening in the gingival surface of the slot 40, as close as possible to the bracket labial surface 32, so as to provide a mesial-distal extending retainer wall 62 that can be engaged by the end 58 when the retainer member is in the slot-closed position. The inner lingual surface of this wall is in this embodiment inclined lingually so that once it is engaged by the labially inclined end of the retainer member the mutual engagement tends to retain the retainer member in the slot-closed position. The labial-lingual depth of the retainer slot is such that the retainer member is able to engage the smallest cross-section arch wire with which the bracket is to be used, such as the round wire 42, and is also able to accommodate the largest cross-section wire that is to be used with a small amount of clearance between it and the wire. Engagement of the retainer member with the special arch wire 44 will move the end 58 to about the middle of the slot, as shown in solid lines in FIG. 2, so that some labial movement of the end is still possible. The maximum possible labial movement is however restricted to a predetermined extent when the end engages the wall 62, as illustrated in broken lines, and this will be within the amount that would result in over-stressing and damage to the springy retainer member.

In this embodiment the wall 62 closing the labial side of the slot 60 is constituted by a small piece 64 of the spring stainless steel used for the retainer member 48, the piece being shaped to conform closely to the contour of the adjacent portion of the body and being welded thereto, e.g. by laser or ultrasonic welding. This material is well suited for the purpose and is readily available. The width of the piece 64 in the mesial distal direction is less than that of the bracket body, so as to permit some rotation of the bracket about the occlusal-gingival axis for application of torque to the tooth without interference between the retainer member and the piece 64. In practical embodiments the width of the bracket will vary between about 1.8 mm and 2.3 mm (0.072 to 0.090 inch) while the width of the piece 64 is about 1 mm (0.040 inch). In this embodiment the piece 64 is simply laid on the surface of the bracket and then welded thereto, but in other embodiments (not illustrated) the piece may be at least partly set into a suitable groove in the body.

In the slot-closed position the straight part of the retainer member labial portion intrudes progressively deeper into the slot in the occlusal to gingival direction, and the extent of this intrusion is made such that it will abut firmly against the arch wire therein. As a result of this relatively deep intrusion into the slot, any movement of the retainer member away from the slot-closed position can only take place against the resilience of the material of the retainer member, particularly of the labial and occlusal parts thereof, owing to the need for the straight labial portion and the opposed lingual portion to move apart from one another in sliding over the body part which they embrace. The resilience of the springy material of the retainer member therefore provides a force at all times urging the retainer member to move to the slot-closed position, where the free edge 58 protrudes into the retainer slot 60.

In the full slot-open position of the retainer member, illustrated in FIG. 2 in broken lines, the labial retainer member free end 58 sits on a mesial-distal extending so-called "parking" groove 64. This groove is a discontinuity in the labial surface portion and is disposed at such an inclination to the remainder of the surface that any force component caused by the retainer member resilience and tending to urge the member to the slot-closed position is not able to move the end off the parking groove, so that the member is retained sufficiently securely in the slot-open position. Usually the parking groove will be located to correspond with the maximum slot-open position. It would usually be sufficient to make the groove 64 parallel to the bracket lingual surface for adequate retention. As illustrated, the shape of the end 58 of the spring is convex toward the body to conform to the shape of the parking groove. The resultant curved end reduces mechanical interference that otherwise can occur between the retainer member and arch wire as the retainer member moves toward the slot-closed position.

In use the brackets selected for the particular procedure are cemented to the respective teeth and one end of the arch wire is locked to the end-most bracket by any suitable means (not illustrated). All the retainer members are placed in the slot-open position, the arch wire is inserted into the slots, if possible, and the retainer members are then moved to the slot-closed positions with the ends 58 protruding into the retainer slots 60. The retainer members are of adequate strength and rigidity to retain the wire in the slots but permit free movement of the bracket along the wire and, with circular cross-sections, will allow various rotations of the bracket relative to the wire. Any force tending to urge the arch wire out of the slot, forces it against the inclined surface of the inwardly-protruding part of the retainer member labial portion, resulting in a force at all times positively urging the retainer member to move to the slot-closed position, the engagement of the retainer member ends 58 with the respective walls 62 eliminating the possibility that under the extremely arduous and unpredictable conditions to which the brackets are subjected, any of the retainer members can spring open and allow the arch wire to escape.

Figure 3:
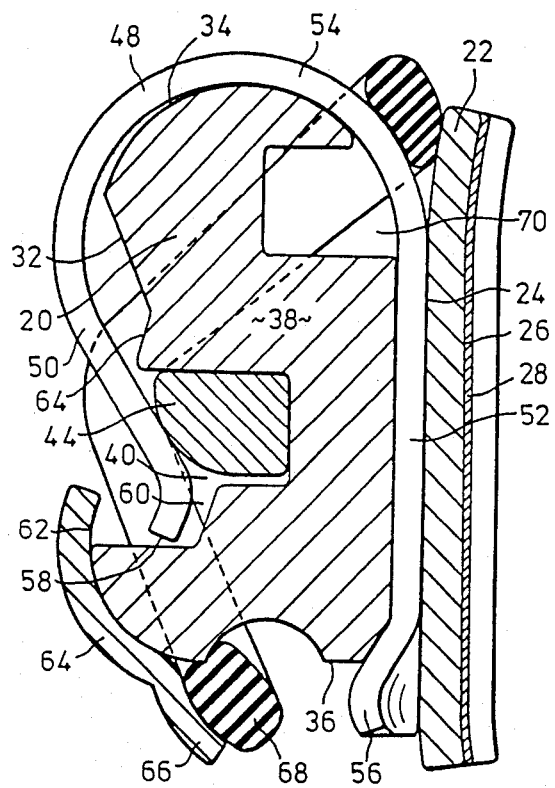
FIG. 3 is a similar view to FIG. 2 of a second embodiment.

In the embodiment illustrated by FIG. 3 the piece 64 extends below the gingival portion of the bracket body at 66 and forms a tie wing which can serve as an anchor for a tie wire (not shown) or an elastomeric band 68 which extends around the arach wire and the junction of the occlusal portion 34 with the base 22.

Figure 4:
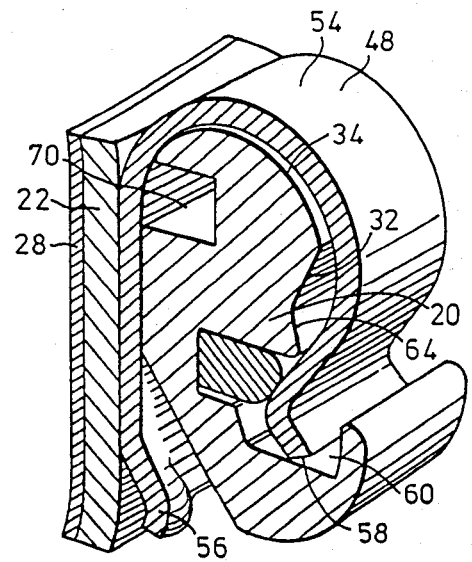
FIG. 4 is a perspective part-sectional view of a third embodiment.

In the embodiment of FIG. 4 the retainer member slot 60 is formed in the bracket body by cutting the slot directly in the metal, so that a separate piece 64 is not required.

Each bracket is also provided with a mesial-distal extending passage 70 of rectangular cross-section at the junction of the body lingual and occlusal surface positions, through which a tie wire can be passed to secure the arch wire to the bracket, for example, if at the start of the procedure the arch wire is so far displaced from the bracket that it cannot be engaged in the arch wire slot 48. This passage 70 can also cooperate with the gingival extending portion 66 of the piece 64 for securing an elastomeric band to the bracket.

I claim:

1. An orthodontic bracket comprising a bracket body having lingual, labial, gingival, occlusal, distal and mesial surface portions and a mesial-distal extending arch wire slot opening to the labial surface portion, and a retainer member of resilient material having labial and lingual portions in embracing sliding engagement with corresponding labial and lingual surface portions of the body, the retainer member being movable on the body between two positions in which the open labial side of the slot is respectively open and closed, wherein the mesial distal extending slot is provided in its gingival surface immediately adjacent to the labial bracket surface with a mesial distal extending retainer against which the end of the retainer member labial portion can engage when in slot-closed position to prevent labial movement of the thus engaged retainer member end of more than a predetermined extent.

2. A bracket as claimed in claim 1, wherein the bracket body is provided in its gingival surface portion with a mesial-distal extending tie slot parallel to the said retainer slot so that the portion of the bracket body between them can function as a tie wing for reception of ties, elastomer rings and the like.

3. A bracket as claimed in claim 1, wherein the retainer is constituted by a slot formed in the gingival surface of the mesial distal extending slot.

4. A bracket as claimed in claim 1, wherein the labial wall of the said retainer is constituted by a separate piece of metal fastened to the bracket body.

5. A bracket as claimed in claim 2, wherein the labial walls of the said retainer and tie slot are constituted by a separate piece of metal fastened to the bracket body.

6. A bracket as claimed in claim 4, wherein the said separate piece of metal is also of spring material.

7. A bracket as claimed in claim 5, wherein the said separate piece of metal is also of spring material.

8. A bracket as claimed in claim 4, wherein the said separate piece of metal is narrower in the mesial distal direction than the bracket body.

9. A bracket as claimed in claim 5, wherein the said separate piece of metal is narrower in the mesial distal direction than the bracket body.

10. A bracket as claimed in claim 1, wherein the end of the retainer member labial portion engaging in the retainer slot is inclined toward the labial, whereby engagement of the inclined end with the lingual wall of the retainer slot tends to retain the retainer member in the slot-closed position.

11. A bracket as claimed in claim 1, wherein the lingual wall of the retainer slot is inclined toward the lingual, whereby engagement of the end of the retainer member labial portion engaging in the retainer slot tends to retain the retainer member in the slot-closed position.

12. A bracket as claimed in claim 8, wherein the lingual wall of the retainer slot is inclined toward the lingual, whereby engagement of the labially inclined end of the retainer member labial portion engaging in the retainer slot tends to retain the retainer member in the slot-closed position.

* * * * *